(12) United States Patent
Rask-Andersen et al.

(10) Patent No.: US 7,498,360 B2
(45) Date of Patent: Mar. 3, 2009

(54) METHOD AND COMPOSITIONS FOR LOCAL TREATMENT OF MENIERE'S DISEASE, TINNITUS AND/OR HEARING LOSS

(75) Inventors: Helge Rask-Andersen, Uppsala (SE); Johan Stjernschantz, Uppsala (SE)

(73) Assignee: Synphora AB, Uppsala (SE)

( * ) Notice: Subject to any disclaimer, the term of this patent is extended or adjusted under 35 U.S.C. 154(b) by 0 days.

(21) Appl. No.: 10/343,789

(22) PCT Filed: Jan. 15, 2002

(86) PCT No.: PCT/SE02/00062

§ 371 (c)(1),
(2), (4) Date: Jun. 5, 2003

(87) PCT Pub. No.: WO02/056890

PCT Pub. Date: Jul. 25, 2002

(65) Prior Publication Data

US 2004/0029970 A1    Feb. 12, 2004

(30) Foreign Application Priority Data

Jan. 19, 2001    (SE) ................... 0100158

(51) Int. Cl.
*A01N 37/08* (2006.01)
*A01N 43/00* (2006.01)
*C07C 59/147* (2006.01)

(52) U.S. Cl. .......... 514/573; 514/530; 514/211.02; 554/117; 554/118; 554/119

(58) Field of Classification Search ............ 514/530, 514/573, 613, 211.02; 424/437; 554/117, 554/118, 119
See application file for complete search history.

(56) References Cited

U.S. PATENT DOCUMENTS 4,946,870 A * 8/1990 Partain et al. ............ 514/777
5,176,654 A    1/1993 Schreiber
5,476,446 A    12/1995 Arenburg
5,510,383 A * 4/1996 Bishop et al. ............ 514/530

FOREIGN PATENT DOCUMENTS

EP    0628545    6/1994

OTHER PUBLICATIONS

Briner, et al., Synthetic Prostaglandin E1 Misoprostol as a Treatment for Tinnitus, 1993, Arch Otolaryngol Head Neck Surg, vol. 119, 652-654.*
International Cosmetic Ingredient Dictionary and Handbook, Seventh Edition, 1997, vol. 1, p. 618.*
Salt et al. (Local inner-ear drug delivery and pharmokinetics, Drug Discovery Today, Reviews, vol. 10, No. 19, pp. 1299-1306, Oct. 2005).*
Escoubet et al. 1985. Prostaglandin Synthesis by the Cochlea of the Guinea Pig Influence of Aspirin, Gentamicin, and acoustic stimulation, Prostaglandins 29(4):589-599.*
Michel O et al. 1992. Effects of prostaglandin E2 on the fluctuating hearing loss in Meniere's disease. Auris Nasus Larynx. 19(1):7-16.*
Briner et al, *Arch Otolaryngol Head Neck Surg.*, vol. 119, pp. 652-654 (1993).
"Misoprostol (Cytotec®) Preclinical and Clinical Review," Physicians and Scientists Publishing Co., Glenview, IL (1990).
Sauer et al., "Prostaglandins in the Guinea Pig Cochlea," Prog. Clin. Biol. Res., 242:131-137 (1987).
Kawata et al. "Prostaglandins Synthesis by the Cochlea," Prostaglandins, 35:173-174 (1988).
J. Nadine Brown, et al, "Osmotic pump implant for chronic infusion of drugs into the inner ear", *Hearing Research*, 70 (1993) 167-172.

* cited by examiner

*Primary Examiner*—Sreeni Padmanabhan
*Assistant Examiner*—Kara R McMillian
(74) *Attorney, Agent, or Firm*—Porter Wright Morris & Arthur LLP

(57) ABSTRACT

A novel method and compositions for the local treatment of Meniere's disease, tinnitus and hearing loss are described. The treatment is based on the administration of a therapeutically effective amount of a prostaglandin of the F-type to the inner ear. The treatment can be either continuous or intermittent and may involve the use of pumps, gels, or slow release drug inserts.

27 Claims, No Drawings

METHOD AND COMPOSITIONS FOR LOCAL TREATMENT OF MENIERE'S DISEASE, TINNITUS AND/OR HEARING LOSS

Related Application

The present application is a Section 371 application of PCT/SE02/00062 filed Jan. 15, 2002.

The present invention concerns a novel method and composition for the treatment of Meniere's disease, hearing loss and tinnitus.

BACKGROUND OF THE INVENTION

Meniere's disease, a disorder of the inner ear, afflicts around 0.1-0.5% of the adult population. The disease is characterized by vertigo, hearing loss and tinnitus, and usually begins in the middle life, although it may manifest itself even at lower age. The disease occurs in both sexes at about the same rate. It typically occurs in episodes of marked vertigo, hearing loss and tinnitus, lasting for hours up to a few days, but also during the intermittent time periods the patients may suffer from tinnitus and hearing loss. Usually Meniere's disease is unilateral, but with time both ears may become involved, and an estimated 12 percent have bilateral disease.

Although the disease tends to be episodic with severe vertigo, nausea and hearing loss and subsequent remissions, with time patients usually suffer from general hearing loss and tinnitus. The remissions may last from a day to several years, but most commonly they last for a few weeks to months. Not uncommonly speech perception is reduced during the attacks. Complete deafness in the affected ear has been reported to occur at a rate of about 10 percent. The individual symptoms of Meniere's disease may vary greatly between patients as may the duration of the remissions, but the disease typically is chronic lasting the whole remaining life from its onset. The disease may impair the working ability and social life of the patients leading to psychological and mental disturbances, and in severe cases patients have even committed suicide because of the disease.

The pathophysiology of Meniere's disease is currently not well understood, but it is generally regarded that the pressure of the endolymphatic fluid of the internal ear is pathologically increased leading to a condition called hydrops (swelling of the membraneous labyrinth including the cochlea of the internal ear due to too high pressure). The increased pressure may cause ruptures of the membranes in the labyrinth reducing the increased pressure and thus alleviating the symptoms of the acute attacks. The anatomy of the internal ear is described below.

In spite of the fact that Meniere's disease is relatively common and disabling there is no causal therapy for the disease. Currently all efforts have to be directed towards symptomatic treatment or to direct destructive treatment of the internal ear by surgical intervention or by administration of ototoxic drugs such as gentamycin into the ear. Thus, Meniere's disease is a significant clinical problem causing much suffering to patients, and consequently a causal therapy for the acute attacks as well as the symptoms during the remissions would be very desirable from a clinical point of view.

Tinnitus, the perception of sound in absence of acoustic stimulus, is a very common disorder amongst middle age and elderly people. As many as 10 percent of the middle age/elderly population may suffer from some degree of tinnitus. Most patients complaining of tinnitus however do not suffer from Meniere's disease, but have a local disorder in the organ of Corti which contains the hair cells. These cells transform mechanic energy into electrochemical energy for propagation of the hearing impulses to the brain. The pathophysiologic ethiology of tinnitus is poorly understood. Various causes of tinnitus may include acoustic trauma leading to permanent destruction e.g. of hair cells in the organ of Corti, microvasculopathies in the cochlea, toxic effects of drugs, and infections. Often tinnitus is associated with a hearing loss, which can be determined by audiometry. There are many variants of tinnitus some of which are caused by disorders in the tympanic membrane and external ear and which often can be successfully treated, but usually tinnitus derived from the inner ear is incurable or difficult to treat.

Hearing loss or hearing impairment, i.e. the inability to perceive the normal range of sounds audible to an individual with normal hearing, is also a very common disorder. Hearing loss may be greater at some frequencies than others, or all frequencies may be equally affected. The etiology of hearing loss is quite complex, and not fully elucidated. Causative factors may be physical damage to the outer or middle ear, acute or chronic acoustic trauma, ageing, damage to the inner ear or the auditory nerve. It is also not uncommon that hearing loss appears as a sequelae to other diseases or as an unwanted side effect of certain pharmaceuticals.

In the present description, examples and claims, the terms hearing loss and tinnitus are used in their widest meaning, as generally understood by a person skilled in the art.

Currently there are no clinically proven remedies for the treatment of tinnitus or hearing loss, and a drug that could be used to prevent, alleviate or eliminate these symptoms would thus be very desirable from a clinical point of view.

Anatomy and Physiology of the Ear

The ear is divided into three main parts; the external ear, the middle ear and the inner ear. The external ear consists of the auricle (pinna) and the ear canal which ends at the tympanic membrane. The middle ear consists of the tympanic membrane, the tympanic cavity, the auditory ossicles and the Eustachian tube. The inner ear, also called the labyrinth because of its complex structure, consists of sacs and tubules suspended in cavities of the petrous portion of the temporal bone. These structures contain a fluid called the endolymph, while the space between the membranous labyrinth and the bone is filled with the perilymph. The bony labyrinth consists of two parts; the vestibule which houses the saccule, the utricle, the semicircular canals, and the cochlea, a spirally coiled structure. The sense of balance is located in the vestibule while the sense of hearing is located in the cochlea.

The cochlea is a two and three quarters coiled cavity in the bone containing a membranous structure filled with fluid. The cochlear membraneous structure comprises three cavities; the scala vestibuli connected to the oval window and the middle ear ossicles; the scala tympani connected to the round window at the middle ear; and finally the scala media or the cochlear duct being part of the endolymphatic system. The scala vestibuli and scala tympani are parts of the perilymphatic system. The scala media contains the sound perceiving organ, the organ of Corti, a complex structure containing hair cells receiving the hydromechanical energy and converting it to electrochemical signals, supporting cells, a basilar membrane and a tectorial membrane as well as nerve fibres connecting the organ to the nearby situated spiral ganglion. From the spiral ganglion nerve fibres project to the brain for further processing of the auditory signals. The scala media also contains a highly vascularized structure called stria vascularis, and it is regarded that the endolymph of the cochlea is formed in this structure.

The sound reaching the tympanic membrane of the middle ear will cause it to vibrate and the energy is then passed on to the oval window of the inner ear through the ossicles. The energy from the oval window causes a pressure wave in the scala vestibuli to be conveyed through the tip of the cochlea through an opening into the scala tympani which is connected to the round window at the middle ear. This pressure wave in the perilymphatic fluid system causes through the basilar membrane the hair cells to vibrate against the tectorial membrane thus transforming mechanical energy into electrochemical energy. Finally most of the energy from the external sound is released from the cochlea into the middle ear through the round window membrane.

The endolymphatic system of the cochlea is connected through ductus reuniens to the endolymphatic system of the sacculus in the vestibular organ. The sacculus is further connected to the utriculus joined by three semicircular canals. The sacculus, utriculus and the semicircular canals have a physiologic function in detecting movements and position and thus relate to the sense of balance. Disorders in this part of the inner ear usually cause symptoms of vertigo often associated with nausea. Both the utriculus and the sacculus are connected through a small canal called the endolymphatic duct to the endolymphatic sac. The endolymphatic duct, a minuscule structure, has a very important function in that the endolymph is believed to be resorbed into the lymphatic and/or blood vessels in this structure.

Thus the endolymph is believed largely, if not totally, to be formed in the stria vascularis of the scala media of the cochlea and the wall of the utriculus. It then slowly flows from the cochlea into the sacculus and utriculus to finally end up in the endolymphatic duct and sac where it is resorbed. The endolymphatic duct is a tiny about 2 mm long narrow canal embedded in loose connective tissue in the corresponding bony canal. Lymphatics and blood vessels run through the loose connective tissue. The endolymphatic duct is lined by a single epithelial cell layer and water and solutes have to traverse this cell layer to enter the loose connective tissue. From here the water is resorbed into the lymphatic vessels or the veins because the intraluminal pressure is negative (estimated to −5 to −10 mmHg) compared to the atmospheric pressure (0 mmHg) in the connective tissue stroma and the endolymphatic duct. Thus it is likely that the driving force for the endolymph to leave the endolymphatic duct is largely the difference in hydrostatic pressure between endolymphatic duct and the lymphatic vessels and veins in the connective tissue stroma. The lymphatic vessels empty into the veins. Oncotic pressure gradients are unknown. It is presently regarded that, in Meniere's disease, the resorption of the fluid is impaired leading to increased pressure in the endolympahtic fluid both in the vestibule and the cochlea resulting in typical symptoms such as vertigo, nausea, hearing impairment and tinnitus.

PRIOR ART

The physiological function of endogenous prostaglandins, particularly $PGE_1$, $PGE_2$ and $PGI_2$ (prostacyclin) in the cochlea has previously been investigated in many studies, and it has been suggested that these arachidonic acid metabolites may be important in the regulation of the cochlear blood flow (see e.g. Umemura et al., 1990; Rhee et al., 1999). While $PGF_{2\alpha}$ has also been shown to be synthesised in cochlear structures of experimental animals, the physiological function of $PGF_{2\alpha}$ remains completely unknown (Escoubet et al., 1985; Kawata et al., 1988; Umemura et al., 1990), and no effect was observed of $PGF_{2\alpha}$ on the vasculature in the cochlea. The finding made by the present inventors, that the receptor for $PGF_{2\alpha}$ (the FP prostanoid receptor) is abundantly distributed in the hair cells and spiral ganglion was therefore very surprising and implies a hitherto unknown function for $PGF_{2\alpha}$ in the cochlea.

Previously prostaglandins have been hypothesised to be involved in the pathophysiological mechanism of a wide variety of diseases such as Meniere's disease, tinnitus, glaucoma, arthritis and bursitis (Rudin, 1980), and indomethacin was found to block the effect of furosemide on the discrimination score of two patients with Meniere's disease possibly suggesting an involvement of undefined prostaglandins in inner ear fluid dynamics (Arenberg and Goodfriend, 1980). Previously it has also been shown in a clinical study that sulprostone, a $PGE_2$ derivative, after 1 hour intravenous infusion produced a short hearing threshold shift similar to that caused by furosemide and it was speculated that $PGE_2$ may be involved in the hearing function (Michel and Matthias, 1992). In addition to this, another synthetic PGE analogue, misoprostol, given systemically has been shown to exert some effect on tinnitus in a clinical study (Brinel et al., 1993). In this study, misoprostol was administered orally.

DESCRIPTION OF THE INVENTION

The present inventors have now unexpectedly found that the local administration of prostaglandins has a highly beneficial effect in the treatment of Meniere's disease, tinnitus and hearing loss. These drugs seem to enhance the resorption of the fluid from the endolymphatic duct thus leading to reduced pressure in the endolymphatic space and an alleviation of the symptoms of Meniere's disease. In addition prostaglandins, at least prostaglandins of the F-type, may have a direct beneficial effect in the cochlea because the present inventors have surprisingly found that the FP prostanoid receptor is abundantly expressed in the cochlear region of the inner ear e.g. in the organ of Corti, the spiral ganglion, and the stria vascularis. This finding is particularly interesting from the point of view that non-steroidal anti-inflammatory drugs (NSAIDs) such as acetylsalicylic acid (aspirin), and indomethacin are known to be ototoxic, and frequently cause tinnitus as side-effect in many patients, and since these drugs block the cyclo-oxygenase enzymes and thus the production of endogenous prostaglandins it is not inconceivable that prostaglandins are important in the cochlea to maintain normal physiological conditions, and that they can be used to treat, alleviate or prevent tinnitus and hearing loss.

Exogenous prostaglandins, particularly of the F-type, derivatives thereof, or prostanoid FP receptor agonists administered to the internal ear may thus help to alleviate tinnitus symptoms. As there is no causal therapy for Meniere's disease, tinnitus and/or hearing loss as of today, the findings disclosed in the present description are regarded as particularly valuable from a clinical point of view. Accordingly, the present invention provides the use of prostanoid FP receptor agonists, for example prostaglandins of the F type, for the treatment of Meniere's disease, tinnitus, and/or hearing loss, as well as specific methods and compositions for this use.

The present inventors have shown abundant expression of the FP prostanoid receptor, but not of the EP prostanoid receptors in the internal ear, and that local application of latanoprost, a $PGF_{2\alpha}$ analogue and FP receptor agonist, has an unexpected alleviating effect on the tinnitus symptom in Meniere's disease in addition to improving hearing ability.

The prostanoid FP receptor is a well defined, cloned, sequenced, and pharmacologically characterized entity. Agonists on the receptor accordingly are compounds (for example prostaglandin analogues) that bind and activate the receptor. Selective agonists on the receptor are compounds (for example prostaglandin analogues) that with preference bind and activate the receptor over other prostanoid receptors, in pharmacological terms usually meaning that the difference in $EC_{50}$ or Kd value between the FP receptor and other prostanoid receptors is at least one log unit.

Prostaglandins are fatty acids usually derived from the precursors eicosatrienoic, eicosatetraenoic (arachidonic) or eicosapentaenoic acid through metabolic steps involving ring closure and oxygenation catalysed by the cyclo-oxygenase enzymes (COX-1 and COX-2). The prostaglandins typically carry a cyclopentane ring to which two carbon chains link, the upper usually being called the alpha chain consisting of 7 carbons including a terminal carboxylic acid moiety, while the lower chain usually is called the omega chain and comprises 8 carbons including a terminal methyl group. The prostaglandins have the general structure:

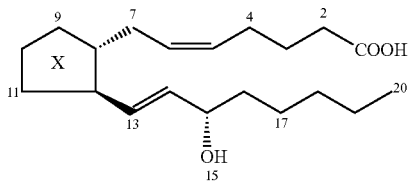

In which the cyclopentane ring (X) may be substituted as shown below:

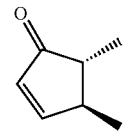 A

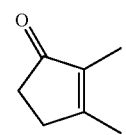 B

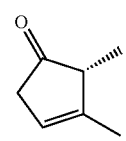 C

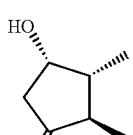 D

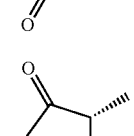 E

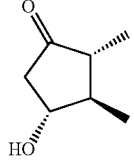

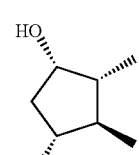 F

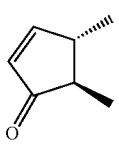 J

Depending on the number of double bonds in the chains subscripts of 1 to 3 are used. In prostaglandins with subscript 1 e.g. $PGF_{1\alpha}$ and $PGE_1$ the double bond is situated between carbons 13 and 14 in the omega chain and exhibits trans configuration in the naturally occurring prostaglandins. In prostaglandins with subscript 2 e.g. $PGF_{2\alpha}$ and $PGD_2$ an additional double bond in the cis configuration is located between carbons 5 and 6 in the alpha chain. In prostaglandins with the subscript 3, a third double bond is situated between carbon 17 and 18 in the omega chain, exhibiting cis configuration in naturally occurring prostaglandins. The hydroxyl group on carbon 15 in prostaglandins is essential for biologic activity and dehydrogenation of the hydroxyl group to keto markedly reduces the activity/potency of the prostaglandins.

Prostaglandins are presently used as medicaments for several different disorders, e.g. for the treatment of gastric ulcer, or for prevention of gastric ulcer during NSAID treatment (misoprostol), for the treatment of impotence (alprostadil), for induction of labour and softening of the cervical tissue in the uterus (E and F prostaglandins), as well as for the treatment of glaucoma (latanoprost and isopropyl unoprostone). In particular, prostaglandin esters e.g. the isopropyl or methyl ester have proven advantageous for increasing the bioavailability as well as for stabilisation of the prostaglandins. While many naturally occurring prostaglandins tend to cause irritation e.g. in the eye when applied locally, prostaglandins with a terminal ring-substitution in the omega chain, preferentially 17-phenyl, or 16 phenoxy derivatives of e.g. $PGF_{2\alpha}$ have been shown to have excellent therapeutic index in the eye (WO89/03384, Stjernschantz and Resul), and such compounds are also preferred in the present invention.

Currently in particular latanoprost (13,14-dihydro-17-phenyl-18,19,20-trinor-$PGF_{2\alpha}$-isopropyl ester), and 16-[(3-trifluormethyl)-phenoxy]-17,18,19,20-tetranor-$PGF_{2\alpha}$-isopropyl ester, 17-phenyl-18,19,20-trinor-$PGF_{2\alpha}$-isopropyl ester, as well as 17-[(3,5-difluoro)-phenyl]-18,19,20-trinor-$PGF_{2\alpha}$ and esters of these analogues are preferred for use in the treatment of Meniere's disease, tinnitus, and/or hearing loss according to the present invention. Prostaglandin related compounds such as prostamides, e.g. AGN192024 (Bimatoprost) and derivatives and analogues of prostaglandins such as travoprost and isopropyl unoprostone are also compounds that fall under the scope of this invention.

Thus the present invention provides a novel method for the treatment of Meniere's disease, tinnitus, and/or hearing loss, wherein a pharmaceutically effective amount of a prostanoid FP receptor agonist, or an F-type prostaglandin, or a derivative thereof is administered locally to the ear. In particular, the round and/or oval window of the inner ear is contacted with a physiologically acceptable composition comprising a pharmaceutically effective amount of a prostanoid FP receptor agonist, or an F-type prostaglandin, or a derivative thereof.

According to one embodiment of the invention, the prostanoid FP receptor agonist is $PGF_{2\alpha}$ or a derivative of $PGF_{2\alpha}$. According to the invention, the prostaglandin can be substituted in the omega chain with an aromatic or non-aromatic ring structure. The prostaglandin is preferably selected from the group consisting of 13,14-dihydro-17-phenyl-18,19,20-trinor-$PGF_{2\alpha}$, 16-[(3-trifluormethyl)-phenoxy]-17,18,19,20-tetranor-$PGF_{2\alpha}$, 17-phenyl-18,19,20-trinor-$PGF_{2\alpha}$, and 17-[(3,5-difluoro)-phenyl]-18,19,20-trinor-$PGF_{2\alpha}$ and alkyl esters and amides thereof.

Most preferably the prostaglandin is selected from the group consisting of latanoprost and latanoprost acid, including pharmaceutically suitable salts thereof.

According to one embodiment of the invention, the prostaglandin is administered in the form of a prodrug. The prostaglandin can for example be administered in the form of an alkyl ester or amide, for example an isopropyl ester or amide, preferably an ethyl amide.

According to the inventive method, a pharmaceutically effective amount of a prostanoid FP receptor agonist, or an F-type prostaglandin, or a derivative thereof is administered to the inner ear 1-100 times a year. According to an embodiment of the invention, said compounds are administered to the inner ear continuously or semi-continuously using a medical pump device or in the form of a gel comprising the prostaglandin and a pharmacologically suitable gel forming substance, carrier or matrix, e.g. hyaluronic acid and/or cross-linked hyaluronic acid.

According to one embodiment of the present invention, said compounds are administered to the inner ear in the form of a slow release drug insert, suitable for placing in the middle air and capable of delivering the active compounds to or in the vicinity of the round and/or oval window.

The present invention provides the use of a prostaglandin of the F-type, a derivative thereof, or a prostanoid FP receptor agonist for the manufacture of a medicament for the treatment of Meniere's disease, tinnitus, and/or hearing loss. According to one embodiment, the prostaglandin is $PGF_{2\alpha}$ or a derivative of $PGF_{2\alpha}$. The prostaglandin can also be a prostaglandin substituted in the omega chain with an aromatic or non-aromatic ring structure. Preferably the prostaglandin is selected from the group consisting of 13,14-dihydro-17-phenyl-18,19,20-trinor-$PGF_{2\alpha}$, 16-[(3-trifluormethyl)-phenoxy]-17,18,19,20-tetranor-$PGF_{2\alpha}$, 17-phenyl-18,19,20-trinor-$PGF_{2\alpha}$, and 17-[(3,5-difluoro)-phenyl]-18,19,20-trinor-$PGF_{2\alpha}$.

Most preferably the prostaglandin is selected from the group consisting of latanoprost and latanoprost acid, including pharmaceutically suitable salts therof. The prostaglandin for the inventive use can also be a prostaglandin in the form of a prostaglandin alkyl ester or amide, for example an isopropyl ester or ethyl amide.

The present invention provides a pharmaceutical composition suitable for local administration for the treatment of Meniere's disease, tinnitus or hearing loss comprising a therapeutically active amount of a prostaglandin of F-type, or a prostanoid FP receptor agonist, and a pharmaceutically acceptable carrier. In this composition, the carrier is preferably a pharmacologically suitable gel forming substance, carrier or a slow release matrix, for example hyaluronic acid or cross-linked hyaluronic acid.

The present invention further provides a device for the treatment of Meniere's disease, tinnitus, and/or hearing loss, wherein said device is capable of releasing a therapeutically effective amount of a prostaglandin, or prostanoid FP receptor agonist in the middle ear of a human patient during a sustained period of time. This device may be a pump for continuous or intermittent, controlled delivery of the above compounds near or at the round and/or oval window.

The invention will be illustrated in closer detail below, in the following non-limiting examples:

EXAMPLES

I. Identification of the FP Prostanoid Receptor in the Inner Ear

Adult albino guinea pigs of either sex weighing 300-500 grams were euthanized with an intraperitoneal injection of a pentobarbital-ethanol solution. The internal ear structures were rapidly dissected out and immersed in 4% fresh formaldehyde solution. The same solution was also perfused through the cochlea and internal ear structures through the oval and round windows. After appropriate fixation the bony tissue underwent decalcification by 8% sodium EDTA treatment for 2-3 weeks. Thereafter the specimens were processed for routine paraffin embedding, and 5-10 µm sections were cut using a microtome. The sections were further processed for immunohistochemistry to demonstrate the FP, $EP_1$ and $EP_3$ prostanoid receptors as well as the COX-1 and COX-2 enzymes. Polyclonal antibodies raised against the first extracellular loop of the human FP, $EP_1$ and $EP_3$ prostanoid receptors were used. To detect the COX-1 enzyme polyclonal antibodies against the ovine COX-1 sequence corresponding to amino acids 272-282 were used, and to detect the COX-2 enzyme polyclonal antibodies raised against the murine COX-2 sequence corresponding to amino acids 584-598, were used.

Immunostaining was performed on paraffin sections, which were dewaxed, rehydrated and incubated with trypsin (0.1%) for 15 min in room temperature. Endogenous peroxidase was blocked with 1% $H_2O_2$ in phosphate buffered saline (PBS) for 30 min in room temperature. After washing in PBS non-specific binding was blocked with 5% normal goat serum (DAKO) for 30 min in room temperature. The primary antibodies were diluted in 0.1% bovine serum albumin in PBS, either 1:250 (for COX-1 and COX-2 detection), or to 8 µg/ml (for FP, $EP_1$ and $EP_3$ receptor detection), and subsequently incubated with the tissue at room temperature for 60 min. As secondary antibodies coupled to peroxidase EnVision+TM (DAKO Readytouse) was used, and the incubation was carried out for 30 min in room temperature. Diaminobenzidine was used as substrate for the peroxidase and the incubation was carried out for around 10 min in room temperature. The slides were counterstained with Mayer Hematoxylin (Histolab) and mounted with coverslip and examined in a light microscope. Appropriate controls without the specific antibodies were included.

In particular the cochlear structures were examined. Staining for both COX-1 and COX-2 was found to be present in the organ of Corti, and many parts of the cochlea. Generally the COX-1 expression seemed stronger than the COX-2 expression. The FP prostanoid receptor was found to be abundantly expressed in the organ of Corti, including the hair cells themselves, in the spiral ligament and stria vascularis as well as in the spiral ganglion. In addition the FP receptor was detected in the endolymphatic duct region. The staining for the $EP_1$ and $EP_3$ prostanoid receptors was much weaker indicating that these receptors are not strongly expressed in the internal ear in contrast to the FP receptor. Thus the FP prostanoid receptor was detected in the most relevant structures with respect to Meniere's disease, tinnitus, and hearing loss, i.e. in the organ of Corti, stria vascularis, the spiral ganglion and the endolymphatic duct region. The fact that the COX enzymes were found to be expressed at least in the cochlea, indicates that endogenous prostaglandins are likely to have a physiological function in the internal ear, which may be of importance e.g. in treating, alleviating or preventing tinnitus symptoms.

2. Demonstration of the Effects of Latanotprost on the Morphology of the Endolymmphatic Duct Structures Four pigmented guinea pigs of either sex weighing around 200-300 grams were anaesthetised with pentobarbital for intratympanic (into the middle ear) administration of latanoprost, and for brain stem audiometric measurements. The audiometric measurements were carried out at 8, 16 and 32 kHz frequency before and after the administration of latanoprost (58 µg/ml; a total of 250 µl/injection corresponding to about 14 µg latanoprost) and the vehicle. Latanoprost was administered once daily for three days into one ear, while the other ear received a similar injection of the vehicle only, and on the fourth day the animals were euthanatized with an overdose of the anaesthetic. The middle ears were dissected and the mucus membranes were inspected. Thereafter the inner ear was removed and the labyrinth was perfusion fixated through the oval and round windows with a 3% buffered glutaraldehyde solution. The tissues were then immersion fixated for about 24 hours in the same solution, and decalcified in 0.1 M sodium EDTA solution for about 2 weeks. The tissues were thereafter prepared according to routine techniques for light microscopy, and ultrathin sections of Epon-embedded tissue pieces were cut for transmission electron microscopy.

No inflammatory changes were detected in the mucous membranes of the middle ear, or in the tympanic membrane in the latanoprost treated or vehicle treated ears, and no morphological changes were detected in the cochlea including the organ of Corti with the hair cells. The brain stem audiograms showed no changes that could be attributed to the treatment with latanoprost or the vehicle. Thus, the mode of administration was technically successful, and latanoprost was well tolerated. Most importantly, in several animals clear-cut changes in the morphology around the endolymphatic duct were detected. These changes comprised a zone of reduced density of the extracellular matrix around fibroblast in the loose connective tissue surrounding the endolymphatic duct. These findings were corroborated by 3 persons. The results indicate that latanoprost has reached the endolymphatic duct and induced the cells to modify the extracellular matrix. Similar effects have previously been seen in the ciliary muscle of the eye after topical treatment with latanoprost and other prostaglandins (Lütjen-Drecoll and Tamm, 1989; Lindsey et al., 1998; Stjernschantz et al., 1998). The results indicate that latanoprost as well as other prostaglandins, at least of the $PGF_{2\alpha}$ type, have the ability to modify the extracellular matrix around the endolymphatic duct which conceivably could reduce the resistance of water flow through the tissue into the lymphatic vessels or the veins, and thus be beneficial in the treatment of Meniere's disease as the pressure in the endolymphatic system would consequently decrease.

3. Demonstration of the Beneficial Effect of Local Administration of Latanoprost to Two Patients Suffering from Meniere's Disease A middle aged female and male patient suffering from unilateral Meniere's disease clinically assessed to be of moderate to severe degree were treated with latanoprost (Xalatan®) once daily for 3 days. About 0.3-0.4 ml of a sterile Xalatan® (0.005% latanoprost) solution was administered by intratympanic installation in close apposition to the round window after appropriate local anaesthesia. The patients were thereafter asked to lie on the side with the treated ear up for about 30 min to enhance the penetration of latanoprost into the internal ear. The patients had at least 40 decibel decrease in the audiogram at 0.5, 1 and 2 kHz frequency, at baseline before treatment with latanoprost. In addition they suffered from episodes of vertigo and nausea in combination with tinnitus. Audiograms, and cochlear emissions were recorded before the treatment and at the 7th or 13th day after the start of the treatment, and information about the subjective symptoms were collected. The audiograms showed no significant change after administration of latanoprost, but the cochlear emissions significantly improved, and the patients experienced a marked improvement in their condition with respect to the tinnitus and hearing ability (Table 1).

TABLE 1

Data obtained in two patients suffering from Meniere's disease before and after treatment with latanoprost.

| Patient | | Male | Female |
|---|---|---|---|
| Age | | 51 | 51 |
| Tinnitus | Before | 3 | 3 |
| | After | 1 | 2 |
| Subjective hearing ability | | Improved | Improved |
| Acoustic emissions (%) | 1 kHz Before | 0 | 0 |
| | After | 45 | 0 |
| | 2 kHz Before | 0 | 0 |
| | After | 0 | 57 |
| | 3 kHz Before | 0 | 0 |
| | After | 42 | 0 |
| | 4 kHz Before | 0 | 0 |
| | After | 0 | 0 |
| | 5 kHz Before | 0 | 0 |
| | After | 0 | 0 |
| Total reproducibility | Before | 5 | 10 |
| | After | 37 | 37 |

Tinnitus was graded as follows: 0 = none, 1 = mild, 2 = moderate, and 3 = marked.
Latanoprost was administered by intratympatic injection once daily for 3 days and the data recorded before the start of the treatment and 7 or 13 days after the start of treatment.

4. Results of First Clinical Trial with Latanoprost in Meniere's Disease

During the priority year, a randomised, double-masked, placebo-controlled clinical trial was performed by the inventors of the present patent application. Nine patients (5 males and 4 females; age 39-65 years) suffering from unilateral Meniere's disease were treated daily for three consecutive days with latanoprost (around 50 micrograms/ml) or placebo adopting a crossover design. Accordingly, each patient was treated with both latanoprost and placebo in random order. Each treatment period lasted for 3 days, and after that the patients were examined at days 5 and 15 from the start of the treatment. Approximately 1 month elapsed between the two treatment periods (washout period). The treatment was given by intratympanic injection (around 0.2-0.8 ml) into the middle ear essentially as described above. Several parameters/symptoms were registered and followed, in particular the following: Pure tone average (decibels), discrimination value (%), tinnitus loudness (decibels), and by using visual analogue scale technique; subjective hearing ability, tinnitus and vertigo. The patients recorded the three last mentioned parameters daily, and the means over the periods 2-5 days and 2-15 days after initiation of treatment with latanoprost and placebo were computed.

In three of the nine patients a marked improvement (25-50%) in discrimination value was observed after treatment with latanoprost. Such improvement was never observed during placebo treatment. At day 15 the mean discrimination value after latanoprost treatment was 68.2±7.2%, while it was 52.9±1.5% after placebo treatment, the difference of 29% being statistically significant at the p<0.05 level. Likewise, a statistically significant (p<0.01) improvement in pure tone average value at day 15 was found after latanoprost treatment in comparison to placebo, the values being 58.9±3.6 and 64.3±3.5 decibels, respectively (a lower value representing improvement). Finally, at least seven out of the nine patients experienced less vertigo both during the immediate period (days 2-5) after initiation of the latanoprost treatment as well as during a longer period (days 2-15) after the initiation of the latanoprost treatment. The values on the visual analogue scale (in mm; decreasing values reflecting improvement, i.e. less sensation of vertigo) were as follows: Days 2-5 latanoprost treatment: 22.4±9.1, and placebo treatment: 33.5±10.8 (p<0.05); Days 2-15 latanoprost treatment: 24.2±10.0 and placebo treatment: 34.2±11.4 (p<0.05). No statistically significant change was observed in tinnitus loudness, subjective experience of tinnitus, or subjective hearing ability, and variable results were obtained in cochlear emissions.

The results of this study, performed by the present inventors, thus demonstrate a positive effect of the prostaglandin both on the hearing process, in particular the ability to discriminate speech, and on the organ of balance, the vestibular apparatus. The fact that the response to latanoprost treatment varied somewhat between the two first patients and the patients included in the clinical trial may be due to different severity of the disease, different time of examination as well as different study design. However, in both studies clear-cut improvement in inner ear function after latanoprost treatment could be observed.

In conclusion, the present inventors have shown in preclinical experiments that the COX enzymes and prostanoid receptors, in particular the FP receptor, are expressed in the relevant structures of the internal ear with respect to Meniere's disease, tinnitus and hearing loss. The present inventors have also shown that intratympanic injection of latanoprost in guinea pigs results in morphological changes in the endolymphatic duct structures reminiscent of increased porosity in the extracellular matrix which can be anticipated to enhance the resorption of endolymphatic fluid. Finally, the present inventors have shown in patients suffering from Meniere's disease a significant clinical improvement after intratympanic latanoprost injection. Thus it is regarded as very likely that prostaglandins have a therapeutic potential in the treatment of patients suffering from Meniere's disease, tinnitus, and hearing loss.

Mode of Administration, Pharmaceutical Compositions, Prostaglandins, and Dosages The preferred mode of administration is by direct instillation through the tympanic membrane, or by slow infusion using a pump into the middle ear. Pharmaceutical compositions comprise the pharmacologically active principle dissolved in compatible vehicles for the use in the middle ear. Such vehicles may comprise aqueous solutions, certain oil solutions, and compatible ointments, but in particular gels based on a synthetic or natural matrix or carrier, e.g. based on hyaluronic acid, or chondroitin sulphate and other glucosamine glycans. In particular crosslinked hyaluronic acid gels to prevent decomposition of the gel are desirable in order to establish a slow release formulation so that the prostaglandin analogue is released into the internal ear during a sustained period of time e.g. during several weeks, or months, or even longer periods. The vehicle furthermore may contain solubilisers, liposomes and physiologically compatible polymers, e.g. polyvinylalcohole, hydroxymethylcellulose, hyaluronic acid, chondroitin sulphate and other glucosaminoglycans, to increase viscosity. Furthermore physiologically compatible nanoparticle formulations may also be employed. The formulations may be preserved with compatible preservatives in suitable concentrations for use in the middle ear.

The present invention accordingly provides the use of analogues of $PGF_{2\alpha}$ and agonists on the FP prostanoid receptor for the treatment of Meniere's disease, tinnitus and hearing loss. In particular latanoprost (13,14-dihydro-17-phenyl-18, 19,20-trinor-$PGF_{2\alpha}$ isopropyl ester), a drug in widespread clinical use for the treatment of glaucoma, and the acid of latanoprost are preferred, including pharmaceutically suitable salts thereof. In addition FP receptor agonists such as fluprostenol and the isopropyl ester of fluprostenol (travoprost), 17-phenyl-18,19,20-trinor-$PGF_{2\alpha}$, and prodrugs thereof, e.g. the isopropyl ester or the ethyl amid (bimatoprost), as well as 17-[(3,5-difluoro)-phenyl]-18,19,20-trinor-$PGF_{2\alpha}$ and esters of this analogue are suitable drug candidates. In particular prostaglandin analogues carrying a terminal aromatic or non-aromatic ring substitution on the omega chain such as a phenyl, biphenyl, furyl, thiophene, cyclopropyl, cyclobutyl, cylopentyl, cyclohexyl, and cycloheptyl on carbon 17, or phenoxy-substituted analogues on carbon 16 are preferred, but $PGF_{2\alpha}$ itself and simpler derivatives and esters of $PGF_{2\alpha}$ may also be suitable.

The dosages of the different prostaglandin analogues vary depending on the intrinsic activity of each analogue but are in the range of 0.01-1000 μg per day, more typically around 1-100 μg. The prostaglandin should preferentially be administered by a slow release system, such as a gel or insert, but injection through tympanic membrane e.g. once daily or once weekly for a certain period of time may also be employed. Continuous administration using an implanted pump device is also possible, and preferable in particular for long term administration of the compounds. Examples of implantable devices include a refillable, post auricular implantable osmotic pump device connected to the middle ear and the area of the round and/or oval window. Typically the prostaglandin should be administered from once daily to a few times a year depending on the duration of the remissions as well as the release properties of the prostaglandin from the composition. Currently it is not known whether the prostaglandin administration should continue also during the remissions or only be given during the attacks of Meniere's disease. However, for the treatment of tinnitus and hearing loss, continuing administration of the prostaglandin in a slow release formulation at regular intervals e.g. 1 to 12 times a year, or more frequently depending on the severity of the disease is considered necessary.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

REFERENCES

Arenberg, I. K. and Goodfriend, T. L. (1980). Indomethacin blocks acute audiologic effects of furosemide in Meniere's disease. Arch. Otolaryngol. 106; 383-386.

Briner, W., House, J, and O'Leary, M. (1993), Synthetic prostaglandin E1 Misoprostol as a treatment for tinnitus, Arch. Otolaryngol Head Neck Surgery, 119: 652-654.

Escoubet, B., Amsallem, P., Ferrary, E. and Tran Ba Huy, P. (1985). Prostaglandin synthesis by the cochlea of the guinea pig. Influence of aspirin, gentamicin, and acoustic stimulation. Prostaglandins. 29; 589-599.

Kawata, R., Urade, Y., Tachibana, M. and Mizukoshi, O. (1988). Prostaglandin synthesis by the cochlea. Prostaglandins. 35; 173-184.

Lindsey, J. and Weinreb, R. N. (1998). Effects of prostaglandins on uveoscleral outflow. In: Uveoscleral outflow. Biology and clinical aspects (Eds. A. Alm and R. N. Weinreb) Mosby-Wolfe Medical Communications. London. pp: 41-55.

Lutjen-Drecoll, E. and Tamm, E. (1989). The effects of ocular hypotensive doses of $PGF_{2\alpha}$-isopropyl ester on anterior segment morphology. In: The ocular effects of prostaglandins and other eicosanoids (Eds. L. Z. Bito and J. Stjernschantz). Progress in Clinical and Biological Research 312. pp: 437-446.

Michel, O. and Matthias, R. (1992). Effects of prostaglandin $E_2$ on the fluctuating hearing loss in Meniere's disease. Auris Nasus Larynx. 19; 7-16.

Rhee, C. K., Park, Y. S., Jung, T. T. and Park, C. I. (1999). Effects of leukotrienes and prostaglandins on cochlear blood flow in the chinchilla. Eur. Arch. Otorhinolaryngol. 256; 479-483.

Rudin, D. O. (1980). Glaucoma, "auditory glaucoma", "articular glaucoma", and the third eye. Med. Hypotheses. 6; 427-430.

Stjernschantz, J., Selén, G., Ocklind, A. and Resul, B. (1998). Effects of latanoprost and related prostaglandin analogues. In: Uveoscleral outflow. Biology and clinical aspects (Eds. A. Alm and R. N. Weinreb) Mosby-Wolfe Medical Communications. London. pp: 57-72.

Umemura, K., Takiguchi, Y., Nakashima, M. and Nozue, M. (1990). Effect of arachidonic acid on the inner ear blood flow measured with a laser Doppler flowmeter. Ann. Otol. Rhinol. Laryngol. 99; 491-495.

The invention claimed is:

1. Method for the treatment of Meniere's disease, tinnitus and/or hearing loss, comprising administering a pharmaceutically effective amount of a $PGF_{2\alpha}$ prostanoid FP receptor agonist locally to the inner ear by a device which delivers the prostanoid FP receptor agonist to the round and/or oval window.

2. Method according to claim 1, wherein the prostanoid FP receptor agonist is substituted in the omega chain with an aromatic or non-aromatic ring structure.

3. Method according to claim 1, wherein the prostanoid FP receptor agonist is selected from the group consisting of 13,14-dihydro-17-phenyl-18,19,20-trinor-$PGF_{2\alpha}$, 16-[(3-trifluromethyl)]phenoxy]-17,18,19,20-tetranor-$PGF_{2\alpha}$, 17-[(3,5-difluoro)-phenyl]-18,19,20-trinor-$PGF_{2\alpha}$, 17-phenyl-18,19,20-trinor-$PGF_{2\alpha}$, and 13,14-dihydro-15-keto-20-ethyl-$PGF_{2\alpha}$.

4. Method according to claim 1, wherein the prostanoid FP receptor agonist comprises latanoprost, latanoprost acid, or a salt thereof.

5. Method according to claim 1, wherein the prostanoid FP receptor agonist is administered in the form of a pharmaceutically suitable salt, ester or amide.

6. Method according to claim 1, wherein the prostanoid FP receptor agonist is administered in the form of a pharmaceutically suitable salt.

7. Method according to claim 1, wherein the prostanoid FP receptor agonist is administered in the form of a pharmaceutically suitable ester or amide.

8. Method according to claim 1, wherein the prostanoid FP receptor agonist is administered in the form of a pharmaceutically suitable alkyl ester or amide.

9. Method according to claim 1, wherein the prostanoid FP receptor agonist is administered in the form of a pharmaceutically suitable amide.

10. A method according to claim 1, wherein a pharmaceutically effective amount of the prostanoid FP receptor agonist is administered locally to the inner ear 1-100 times a year.

11. A method according to claim 1, wherein a pharmaceutically effective amount of the prostanoid FP receptor agonist is administered locally to the inner ear continuously by a medical pump device which delivers the prostanoid FP receptor agonist to the round and/or oval window.

12. A method according to claim 1, wherein a pharmaceutically effective amount of the prostanoid FP receptor agonist is administered locally to the inner ear by an injection device.

13. A method according to claim 1, wherein a pharmaceutically effective amount of the prostanoid FP receptor agonist is administered locally to the inner ear by an intratympanic installation device.

14. A method according to claim 1, wherein the prostanoid FP receptor agonist is in the form of a gel or a slow release drug insert.

15. A method according to claim 14, wherein the prostanoid FP receptor agonist is in the form of a gel further comprising hyaluronic acid and/or crosslinked hyaluronic acid.

16. Method for the treatment of Meniere's disease, tinnitus and/or hearing loss, comprising administering a pharmaceutically effective amount of an F-type prostaglandin prostanoid FP receptor agonist comprising $PGF_{2\alpha}$ locally to the inner ear by a medical pump device, by an injection device, or by an intratympanic installation device, which delivers the F-type prostaglandin prostanoid FP receptor agonist to the round and/or oval window.

17. Method according to claim 16, wherein the F-type prostaglandin prostanoid FP receptor agonist is selected from the group consisting of 13,14-dihydro-17-phenyl-18,19,20-trinor-$PGF_{2\alpha}$, 16-[(3-trifluromethyl)]phenoxy]-17,18,19,20-tetranor-$PGF_{2\alpha}$, 17-[(3,5-difluoro)-phenyl]-18,19,20-trinor-$PGF_{2\alpha}$, 17-phenyl-18,19,20-trinor-$PGF_{2\alpha}$, and 13,14-dihydro-15-keto-20-ethyl-$PGF_{2\alpha}$.

18. Method according to claim 16, wherein the F-type prostaglandin prostanoid FP receptor agonist comprises latanoprost, latanoprost acid, or a salt thereof.

19. Method for the treatment of Meniere's disease, tinnitus and/or hearing loss, comprising administering a pharmaceutically effective amount of a $PGF_{2\alpha}$ prostanoid FP receptor agonist locally to the inner ear by delivery of the F-type prostaglandin prostanoid FP receptor agonist to the round and/or oval window.

20. Method according to claim 19, wherein the prostanoid FP receptor agonist is selected from the group consisting of 13,14-dihydro-17-phenyl-18,19,20-trinor-$PGF_{2\alpha}$, 16-[(3-trifluromethyl)]phenoxy]-17,18,19,20-tetranor-$PGF_{2\alpha}$, 17-[(3,5-difluoro)-phenyl]-18,19,20-trinor-$PGF_{2\alpha}$, 17-phenyl-18,19,20-trinor-$PGF_{2\alpha}$, and 13,14-dihydro-15-keto-20-ethyl-$PGF_{2\alpha}$.

21. Method according to claim 19, wherein the prostanoid FP receptor agonist comprises latanoprost, latanoprost acid, or a salt thereof.

22. Method according to claim 19, wherein the prostanoid FP receptor agonist is administered in the form of a pharmaceutically suitable salt, ester or amide.

23. Method for the treatment of tinnitus, comprising administering a pharmaceutically effective amount of an F-type prostaglandin prostanoid FP receptor agonist selected from the group consisting of 13,14-dihydro-17-phenyl-18,19,20-trinor-PGF$_{2\alpha}$, 16-[(3-trifluromethyl)]phenoxy]-17,18,19,20-tetranor-PGF$_{2\alpha}$, 17-[(3,5-difluoro)-phenyl]-18,19,20-trinor-PGF$_{2\alpha}$, 17-phenyl-18,19,20-trinor-PGF$_{2\alpha}$, and 13,14-dihydro-15-keto-20-ethyl-PGF$_{2\alpha}$, and esters and amides thereof, and salts thereof, locally to the inner ear by a medical pump device, by an injection device, or by an intratympanic installation device, which delivers the F-type prostaglandin prostanoid FP receptor agonist to the round and/or oval window.

24. A method according to claim 23, wherein the F-type prostaglandin prostanoid FP receptor agonist is an isopropyl ester of 13,14-dihydro-17-phenyl-18,19,20-trinor-PGF$_{2\alpha}$, or a salt thereof.

25. Method for the treatment of Meniere's disease, comprising administering a pharmaceutically effective amount of a PGF$_{2\alpha}$ prostanoid FP receptor agonist locally to the inner ear by delivery of the F-type prostaglandin prostanoid FP receptor agonist to the round and/or oval window.

26. Method according to claim 25, wherein the prostanoid FP receptor agonist is selected from the group consisting of 13,14-dihydro-17-phenyl-18,19,20-trinor-PGF$_{2\alpha}$, 16-[(3-trifluromethyl)]phenoxy]-17,18,19,20-tetranor-PGF$_{2\alpha}$, 17-[(3,5-difluoro)-phenyl]-18,19,20-trinor-PGF$_{2\alpha}$, 17-phenyl-18,19,20-trinor-PGF$_{2\alpha}$, and 13,14-dihydro-15-keto-20-ethyl-PGF$_{2\alpha}$.

27. Method according to claim 25, wherein the prostanoid FP receptor agonist comprises latanoprost, latanoprost acid, or a salt thereof.

* * * * *